Patent …

United States Patent [19]
Klingenbeck

[11] Patent Number: 4,995,107
[45] Date of Patent: Feb. 19, 1991

[54] COMPUTER TOMOGRAPHY APPARATUS WITH AXIALLY DISPLACEABLE DETECTOR ROWS

[75] Inventor: Klaus Klingenbeck, Nuernberg, Fed. Rep. of Germany

[73] Assignee: Siemens Aktiengesellschaft, Berlin and Munich, Fed. Rep. of Germany

[21] Appl. No.: 408,068

[22] Filed: Sep. 15, 1989

[30] Foreign Application Priority Data

Oct. 17, 1988 [EP] European Pat. Off. ......... 88117262.1

[51] Int. Cl.$^5$ ............................................. G01N 23/00
[52] U.S. Cl. .......................................... 378/7; 378/19
[58] Field of Search ................................. 378/7, 10, 19

[56] References Cited

U.S. PATENT DOCUMENTS 3,937,965 2/1976 Vasseur .
4,149,080 4/1979 Schittenhelm .
4,176,280 11/1979 Greschat et al. .

FOREIGN PATENT DOCUMENTS 2005953 4/1979 United Kingdom .

Primary Examiner—Craig E. Church
Attorney, Agent, or Firm—Hill, Van Santen, Steadman & Simpson

[57] ABSTRACT

A computer tomography apparatus includes an x-ray source which irradiates an examination subject, thereby producing attenuated primary radiation, and scatter radiation. A row of detector elements for the attenuated primary radiation is, during normal operation, disposed behind the examination subject in registry with the x-ray beam. During an examination, the x-ray source and the detector row are rotated around an axis to irradiate the examination subject from different directions. A second row of detector elements, for detecting the scatter radiation, is, during normal operation, disposed next to the primary radiation detector row in the direction of the axis of rotation. During calibration using a standardized scatter element as the examination subject, the primary radiation detector row can be axially displaced to occupy the position normally occupied by the scatter radiation detector row. After calibration, the detector rows are axially displaced in the opposite direction so as to return to their normal operating positions.

1 Claim, 1 Drawing Sheet

COMPUTER TOMOGRAPHY APPARATUS WITH AXIALLY DISPLACEABLE DETECTOR ROWS

BACKGROUND OF THE INVENTION

1. Field of the Invention

The present invention is directed to a computer tomography apparatus, and in particular to a computer tomography apparatus having a row of primary radiation detectors with a row of scattered radiation detectors disposed adjacent thereto in the axial direction of the apparatus.

2. Description of the Prior Art

Computer tomography devices are known which produce transverse tomograms of an examination subject. Such devices have an x-ray source which generates a fan-shaped x-ray beam which penetrates an examination subject. The cross-sectional extent of the x-ray beam in the slice plane is equal to the desired slice thickness. Primary radiation attenuated by the examination subject, as well as scatter radiation, are generated by the passage of the x-radiation through the examination subject. A rotatory mechanism rotates the x-ray source and the detector rows around an axis of rotation so that the examination subject is irradiated by x-rays from different directions. The outputs of the detector rows are supplied to a computer, which constructs an image of the desired slice of the examination subject from the detector signals. The scatter radiation detected by the second row of detector elements is used to correct the signals of the row of primary radiation detector elements.

So-called "third generation" computer tomography devices have a detector row which is rigidly connected to the x-ray source, and which rotates around the examination subject. The detector elements of the detector row can be shielded against scatter radiation generated by the examination subject. Such shielding is accomplished by collimator plates directed at the focus of the x-ray source, and consisting of highly radiation-absorbent material. These collimator plates, given imperfect alignment of the x-ray source and the collimator plates or given fluctuations of the focal position due to thermal influences, cause a shadow to be cast on the detector elements, thereby resulting in a geometrical filling degree below the nominal grid dimension of the detector row during actual operation.

So-called "fourth generation" computer tomography devices have a stationary detector ring (or partial ring) which surrounds the measuring field in which the examination subject is disposed. In these types of computer tomography devices, collimation of the detector elements is not possible, or would be so technologically complex as to be impracticable. Even if collimation could be accomplished in fourth generation computer tomography devices, the same diminution in the filling factor would result.

It is known that a measurement of the scatter radiation outside of the actual tomograph slice correlates, with a good approximation, to the actual scatter radiation measured within the slice.

A computer tomography apparatus is described in German Pat. No. OS 26 42 846, corresponding to U.S. Pat. No. 4,149,080, wherein the scatter radiation outside of the actual tomograph slice is measured by a second detector row, and the output signals of the second detector row are used in the construction of the displayed image of the examination slice.

SUMMARY OF THE INVENTION

It is an object of the present invention to provide a computer tomography apparatus wherein calibration of the detector elements of the second detector row, which measures the scatter radiation, is possible in a simple manner such that the scatter radiation which is incident on the primary radiation detector row can be precisely identified and thereby used to correct for scatter radiation constituents in the measured values from the primary radiation detector row.

The above object is achieved in accordance with the principles of the present invention in a computer tomography apparatus wherein the primary radiation detector row and the scatter radiation detector row are disposed side-by-side in the axial direction of the apparatus, and wherein the primary radiation detector row can, during a calibration operation, be displaced to the position which is occupied by the second detector row during normal operation.

During normal operation of the computer tomography apparatus, the additional detector elements, which form the second detector row and only receive scatter radiation produced by the examination subject, are disposed outside of the tomographic slice by a prescribed axial distance from the primary radiation detector row. The primary radiation detector row and the scatter radiation detector row are together displaceable, so that the primary radiation detector row can, during calibration, be moved to a position at which only scatter radiation is acquired. A standardized scattering element is then used to conduct a simple calibration of the detector elements of the second detector row, which normally measures only the scatter radiation, by means of the calibration conducted with the primary radiation detector row in the position normally occupied by the scatter radiation detector row.

DESCRIPTION OF THE PREFERRED EMBODIMENTS

Figure 1:
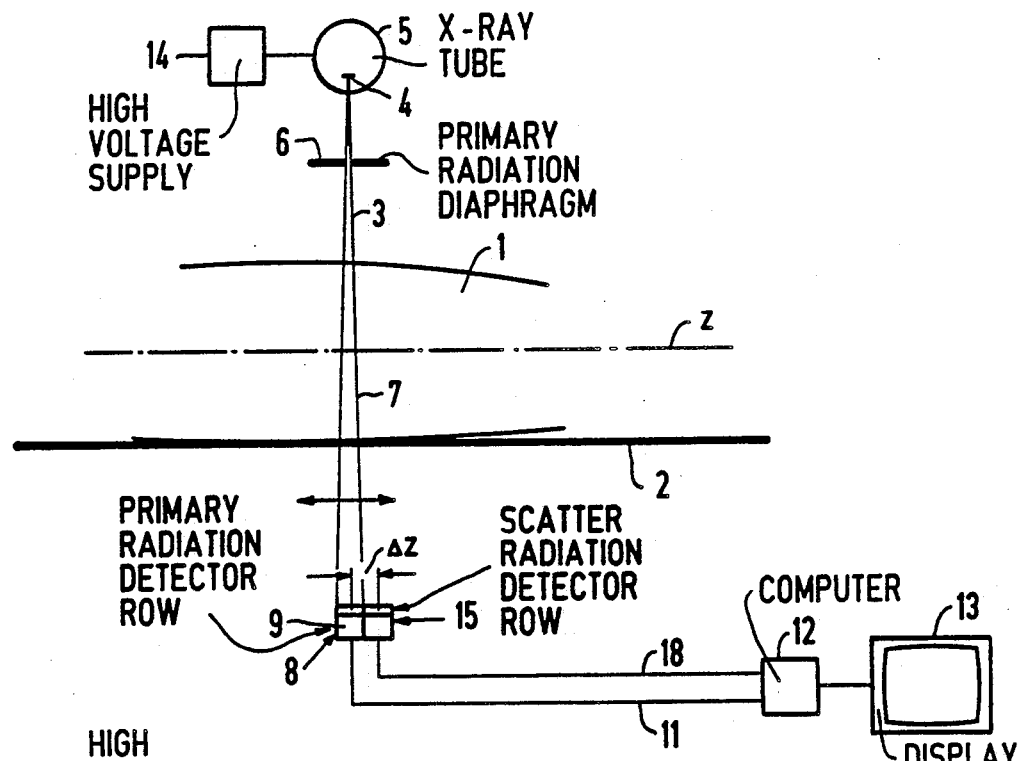
FIG. 1 is a cross-sectional view of selected components of a computer tomography apparatus constructed in accordance with the principles of the present invention.
Figure 2:
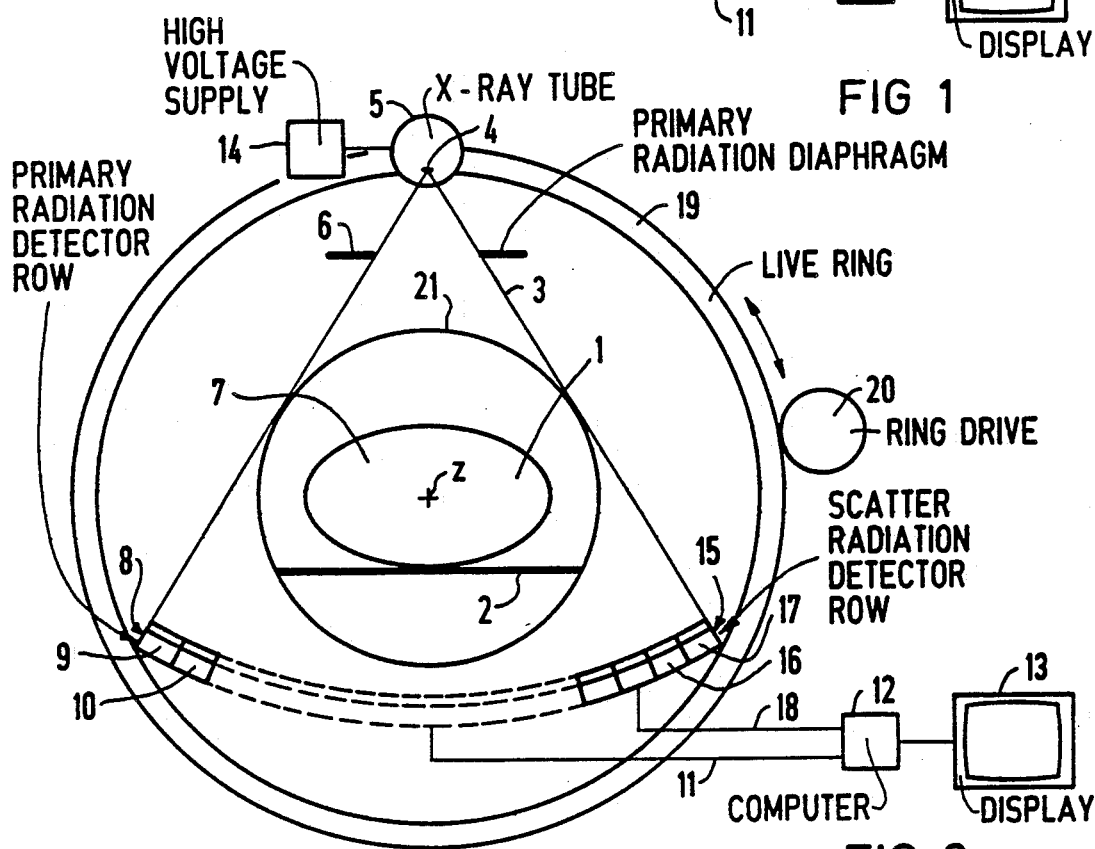
FIG. 2 is a front elevational view of selected components of the tomography apparatus of FIG. 1.

As shown in FIGS. 1 and 2, an examination subject, shown in side view in FIG. 1 and in cross section in FIG. 2, lies on a patient support 2, and is transirradiated by a fan-shaped x-ray beam 3 emanating from a focus 4 of an x-ray tube 5. The x-ray tube 5 is fed from a high voltage supply 14. The x-radiation emanating from the x-ray tube 5 is gated by a primary radiation diaphragm 6 such that the cross-sectional extent of the x-ray beam perpendicular to a body slice 7 being examined is equal to the slice thickness. The x-ray beam 3 is tangential to a measuring field 21 in which the examination subject 1 is disposed.

As seen in the direction of radiation propagation, a primary radiation detector row 8 is disposed behind the examination subject 1. The primary radiation detector row 8 consists of a plurality of detector elements 9, 10, etc. arranged in a row. The number of such detector elements within the primary radiation detector row 8 may be, for example, 512. These detectors detect primary radiation attenuated by the examination subject. The x-ray tube 5 and the primary radiation detector row 8 are mounted on a live ring 19. To obtain an image of the examination subject 1, i.e., the slice 7 thereof, the live ring 19, with the x-ray tube 5 and the detector row 8 thereon, is rotated around an axis z through 360° in either direction of the double arrow shown in FIG. 2 around the examination subject 1. The output signals supplied by the individual detector elements 9, 10, etc. are supplied via line 11 to a computer 12 which calculates an image of the transirradiated slice 7. This image is visually reproduced on a display 13.

The tomography apparatus is additionally provided with a scatter radiation detector row 15. The scatter radiation detector row 15 consists of a plurality of detector elements 16, 17 etc. disposed next to the primary radiation detector row 8 in the axial direction z. The scatter radiation detector row 15 is also mounted on the live ring 19, and rotates around the examination subject 1 during a measurement together with the primary radiation detector row 8. The scatter radiation detector row 15 does not acquire the primary radiation, but only acquires the scatter radiation. It is known that the scatter radiation incident on the detector row 15 during an examination is substantially the same as the scatter radiation incident on the primary radiation detector row 8 used for obtaining the actual measurement signals. Such a measurement is undertaken after implementing the calibration steps described below. The dimensions, position and total number of detector elements in the scatter radiation detector row 15 may differ in comparison to the primary radiation detector row 8. The output signals from the scatter radiation detector row 15 are supplied via a line 18 to the computer 12. The computer 12 contains a circuit which corrects the output signals from the primary radiation detector row 8 by an amount determined by the output signals from the scatter radiation detector row 15, essentially by subtracting, or otherwise compensating for, that constituent of the output signals of the detector row 8 which are assumed to result from scatter radiation incident on the detector row 8.

The scatter radiation detector row 15 need not have the same number of detector elements as the primary radiation detector row 8. It is sufficient for a correction of the output signals of the primary radiation detector row 8 to have a number of detector elements in the scatter radiation detector row 15 which is considerably lower than the number of detector elements in the primary radiation detector row 8.

As is shown in FIG. 1, the two detector rows 8 and 15 are axially displaceable by a distance $\Delta z$, i.e., in the direction of the z axis. Due to the displaceability of the detector rows 8 and 15, the primary radiation detector row 8 can be moved into the position occupied during normal operation by the detector row 15, in which only scatter radiation is acquired, because this position is outside of the slice 7.

Calibration of the detector elements 16, 17 etc. of the scatter radiation detector row 15 can thus be implemented using a standardized scattering object, for example, a uniform circular disk, in the following way. In a first step, the detector elements 9, 10 etc. of the primary radiation detector row 8 are calibrated relative to each other with primary radiation in a known manner, without the scattering object being present in the x-ray beam.

In a second step, the standardized scattering object is moved into the x-ray beam path, and the primary radiation detector row 8 is axially displaced by the distance $\Delta z$, so that the primary radiation detector row now receives the scatter radiation which will be later measured during an actual examination at this same location by the scatter radiation detector row 15.

The measured values acquired in this manner can be referenced $M_i (i=1, \ldots, N_M)$, wherein $N_M$ denotes the number of detector elements 16, 17 etc. The detector row 8, as noted above, may have many more detector elements, however, only the $N_M$ measured values from detector elements which are disposed opposite a detector element of the detector row 15 in the ray fan, i.e., in the azimuthal direction, are used.

In a last step, the entire detector arrangement (i.e., both detector rows) is again moved to the original axial position, and the scatter radiation of the scattering object is again measured using the detector elements 16, 17 etc. of the scatter radiation detector row 15. These measured values can be referenced $M_i (i=1, \ldots, N_M)$.

Calibration factors $E_i = M_i/M_i$ are thus known, with which the measured values of the detector elements 16, 17 etc. during an actual operation are to be multiplied in order to obtain the scatter radiation received by the individual elements of the primary radiation detector row 8. The scatter radiation in the tomographic slice can thus be precisely determined from measured values outside the slice. By subtracting the intensities of the scatter radiation for each element identified in this manner from the measured values of the elements of the detector row 8, the actual primary radiation can be so precisely identified that the tomograms reconstructed using standard methods are free of scatter radiation artifacts.

The calibration method need not be implemented with every change of examination subject. The calibration factors can be stored in a memory as a table, and can be read out for subsequent exposures so that the subsequent exposures can be corrected as described above.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for operating a computer tomography apparatus having an x-ray source which generates a fan-shaped x-ray beam adapted to penetrate an examination subject in a slice plane, the passage of said x-ray beam through said examination subject generating attenuated primary radiation, a row of primary radiation detector elements disposed in said slice plane in an original position for, during an examination, receiving primary radiation attenuated by the patient, and a row of scatter radiation detector elements disposed in an original position out of said slice plane and next to, in the axial direction, said row of primary radiation detector elements so that each scatter radiation detector element has a corresponding axially adjacent primary radiation detector element, for receiving scatter radiation during an examination, said method comprising the steps of:

energizing said x-ray source with said row of primary radiation detectors and said row of scatter radiation detector elements in their respective original positions;

axially displacing said row of primary radiation detector elements and said row of scatter radiation detector elements so that said row of primary radiation detector elements occupies the original position of said row of scatter radiation detector elements;

placing a standardized scattering object in the path of said x-ray beam;

energizing said x-ray source with said standardized scattering object in said x-ray beam, said row of primary radiation detector element receiving scatter radiation, to obtain a first calibration value for each detector in the row of primary radiation detector elements;

returning said row of primary radiation detector elements and said row of scatter radiation detector element to their respective original positions;

energizing said x-ray source with said standardized scattering object in said x-ray beam to obtain second calibration values for each detector in said row of scatter radiation detector element;

placing a patient in the path of said x-ray beam;

conducting an examination of said patient by rotating said x-ray source, said row of primary radiation detector elements and said row of scatter radiation detector elements around said patient so that said patient is irradiated by said x-ray beam from a plurality of different angles, and thereby obtaining an examination radiation value from detector in said row of primary radiation detector elements and from each detector in said row of scatter radiation detector elements;

multiplying each of said examination radiation values from said detectors in said row of scatter radiation detector elements by a factor which is the ratio of said first and second calibration values to obtain a product; and subtracting the product obtained for a scatter radiation detector element from the examination value from its corresponding primary radiation detector element to obtain an actual radiation value.

* * * * *